(12) United States Patent
Liu et al.

(10) Patent No.: US 11,389,644 B2
(45) Date of Patent: Jul. 19, 2022

(54) SELECTIVE CHEMICAL BATH DEPOSITION OF IRIDIUM OXIDE ON THIN FILM FLEXIBLE SUBSTRATES

(71) Applicants: THE REGENTS OF THE UNIVERSITY OF CALIFORNIA, Oakland, CA (US); NATIONAL CHIAO TUNG UNIVERSITY, Hsinchu (TW)

(72) Inventors: Wentai Liu, Los Angeles, CA (US); Chih-Wei Chang, Los Angeles, CA (US); Pu-Wei Wu, Chu-Bei (TW); Chung-Yu Wu, Hsin-Chu County (TW); Po-Chun Chen, Tapei (TW); Tsai-Wei Chung, Tou-Fen (TW)

(73) Assignees: THE REGENTS OF THE UNIVERSITY OF CALIFORNIA, Oakland, CA (US); NATIONAL CHIAO TUNG UNIVERSITY, Hsinchu (TW)

( * ) Notice: Subject to any disclaimer, the term of this patent is extended or adjusted under 35 U.S.C. 154(b) by 6 days.

(21) Appl. No.: 16/404,041

(22) Filed: May 6, 2019

(65) Prior Publication Data
US 2019/0329029 A1    Oct. 31, 2019

Related U.S. Application Data

(63) Continuation of application No. PCT/US2017/060712, filed on Nov. 8, 2017.
(Continued)

(51) Int. Cl.
*A61N 1/05* (2006.01)
*A61N 1/375* (2006.01)
(Continued)

(52) U.S. Cl.
CPC ....... *A61N 1/0551* (2013.01); *A61N 1/37514* (2017.08); *C23C 18/06* (2013.01);
(Continued)

(58) Field of Classification Search
CPC .... A61N 1/0551; A61N 1/37514; A61N 1/05; A61N 1/32; H01L 21/84
See application file for complete search history.

(56) References Cited

U.S. PATENT DOCUMENTS 4,717,581 A * 1/1988 Robblee ............... A61N 1/05
427/126.5
2006/0286725 A1  12/2006 Cheng
(Continued)

FOREIGN PATENT DOCUMENTS

WO    WO2016/033372    *  3/2016    ............... A61N 1/05

OTHER PUBLICATIONS

Chen et al., Chemical Bath Deposition of IrO2 Films on ITO Substrate, Ceramics International, vol. 40, pp. 14983-14990 (Year: 2014).*
(Continued)

*Primary Examiner* — Dah-Wei D. Yuan
*Assistant Examiner* — Andrew J Bowman
(74) *Attorney, Agent, or Firm* — O'Banion & Ritchey LLP; John P. O'Banion

(57) ABSTRACT

A flexible thin film metal oxide electrode fabrication methods and devices are provided and illustrated with thin film polyimide electrode formation and IrOx chemical bath deposition. Growth factors of the deposited film such as film thickness, deposition rate and quality of crystallites can be controlled by varying the solution pH, temperature and component concentrations of the bath. The methods allow for selective deposition of IrOx on a flexible substrate (e.g. polyimide electrode) where the IrOx will only coat onto an
(Continued)

exposed metal area but not the entire device surface. This feature enables the bath process to coat the IrOx onto every individual electrode in one batch, and to ensure electrical isolation between channels. The ability to perform selective deposition, pads for external connections will not have IrOx coverage that would otherwise interfere with a soldering/bumping process.

13 Claims, 6 Drawing Sheets

Related U.S. Application Data

(60) Provisional application No. 62/419,538, filed on Nov. 9, 2016.

(51) Int. Cl.
  *C23C 18/06* (2006.01)
  *C23C 18/12* (2006.01)

(52) U.S. Cl.
  CPC ...... *C23C 18/1216* (2013.01); *C23C 18/1225* (2013.01); *C23C 18/1283* (2013.01)

(56) References Cited

U.S. PATENT DOCUMENTS

2007/0038267 A1  2/2007  Shodo
2015/0367124 A1  12/2015  Noda

OTHER PUBLICATIONS

ISA/US, United States Patent and Trademark Office, International Search Report and Written Opinion dated Jan. 9, 2018, related PCT international application No. PCT/US2017/060712, pp. 1-8 , claims searched, pp. 9-12.

Chen, Jing-Yu et al., "Chemical bath deposition of IrO2 films on ITO subslale". Ceramics International 40 (2014) 14983-14990, published online Jun. 25, 2014.

Chen, Yong-Min et al., "A cost-effective fabrication of iridium oxide films as biocompatible electrostimulation electrodes for neural interface applications", Journal of Alloys and Compounds, vol. 692, Jan. 15, 2017, pp. 339-345 (Absract Only).

Chung, Tsai-Wei et al., "Fabrication of Iridium Oxide/Platinum Composite Film on Titanium Substrate for High Performance Neurostimulation Electrodes", Coatings 2018, 8, 420, published Nov. 23, 2018, 8 pages.

Chen, Yong-Min et al., "A cost effective fabrication of iridium oxide films as biocompatible electrostimulation electrodes for neural interface applications", Journal of Alloys and Compounds 692 (2017) 339-345, published online Sep. 8, 2016.

* cited by examiner

SELECTIVE CHEMICAL BATH DEPOSITION OF IRIDIUM OXIDE ON THIN FILM FLEXIBLE SUBSTRATES

CROSS-REFERENCE TO RELATED APPLICATIONS

This application claims priority to, and is a 35 U.S.C. § 111(a) continuation of, PCT international application number PCT/US2017/060712 filed on Nov. 8, 2017, incorporated herein by reference in its entirety, which claims priority to, and the benefit of, U.S. provisional patent application Ser. No. 62/419,538 filed on Nov. 9, 2016, incorporated herein by reference in its entirety. Priority is claimed to each of the foregoing applications.

The above-referenced PCT international application was published as PCT International Publication No. WO 2018/089545 A1 on May 17, 2018, which publication is incorporated herein by reference in its entirety.

STATEMENT REGARDING FEDERALLY SPONSORED RESEARCH OR DEVELOPMENT

Not Applicable

NOTICE OF MATERIAL SUBJECT TO COPYRIGHT PROTECTION

A portion of the material in this patent document may be subject to copyright protection under the copyright laws of the United States and of other countries. The owner of the copyright rights has no objection to the facsimile reproduction by anyone of the patent document or the patent disclosure, as it appears in the United States Patent and Trademark Office publicly available file or records, but otherwise reserves all copyright rights whatsoever. The copyright owner does not hereby waive any of its rights to have this patent document maintained in secrecy, including without limitation its rights pursuant to 37 C.F.R. § 1.14.

INCORPORATION-BY-REFERENCE OF COMPUTER PROGRAM APPENDIX

Not Applicable

BACKGROUND

1. Technical Field

The technology of this disclosure pertains generally to patterned thin film formation methods, and more particularly to methods for selective deposition of Iridium Oxide (IrOx) on flexible substrates. The fabrication of flexible electrodes using the selective deposition methods is also provided.

2. Background Discussion

Neurostimulation technology can improve the quality of life quality of individuals who are severely paralyzed or have sensory loss and can provide a permanent reduction in severe, chronic pain which would otherwise require constant, high-doses of pain medication.

Medical devices utilizing forms of electrostimulation for treatment of neural diseases require electrodes with electroactive and biocompatible interface materials to transmit signals from the electrodes to the targeted tissues. Implantable neurostimulation electrodes must be able to transmit signals without any secondary effects related to charge transfer at the electrode interface. Neurostimulation electrodes implanted in biological systems are also limited because of the need to operate at a safe voltage to keep cells viable and to prevent unnecessary damage to surrounding tissues.

Electrode surface materials used in neural systems are commonly classified into two distinct categories depending upon the charge transfer mechanism at the electrode interface. The first category is capacitive charge injection materials including gold, titanium nitride and tantalum oxide. The second category is for faradaic charge injection materials such as platinum, platinum/iridium alloy, iridium oxide, and PEDOT.

Between these two categories, the faradaic mechanism has been found to have better charge injection performance than the capacitive mechanism. Of the faradaic charge injection materials, iridium oxide is an attractive ceramic material for neurostimulation electrodes due to its desirable stability and biocompatibility. Iridium oxide has also been shown to be able to provide stimulation by electrochemical reduction and oxidation reactions at the electrode interface without damaging surrounding tissues.

Iridium oxide is typically formed from Iridium (Ir) metal by various techniques including, thermal decomposition (TIROF), reactive sputtering (SIROF), and electrochemical activation (AIROF). Alternatively, iridium oxide films can also be synthesized from iridium salt solutions by electrodeposition (EIROF).

However, these techniques have some undesirable limitations. For example, charge leakage has been seen with sputtered iridium oxide electrodes due to poor adhesion and denseness, which commonly occurs at the edge of the coating layer. Target poisoning, negative thermal effects and ion bombardment are other problems encountered by these deposition techniques. These processes may also have aspect ratio limitations.

Prior art fabrication methods are also limited to selective deposition of $IrO_2$ on solid and rigid substrates such as $Si/SiO_2$ or ITO coated glass etc. Unfortunately, each type of substrate exhibits different chemical properties and their tolerance toward acidity/alkalinity differ greatly. Therefore, a different formulation for deposition is required for use with flexible substrates. Substrates also differ in their tolerance for high temperatures that may be required for some deposition techniques.

Accordingly, there is a need for new electrode deposition methods that do not have the chemical, temperature or aspect ratio limitations of existing methods.

BRIEF SUMMARY

The present technology provides devices and methods of flexible IrOx electrode fabrication comprising thin film polyimide electrode formation and IrOx chemical bath deposition. For iridium oxide films, final redox states, charge storage capacities, and impedances at the interface are highly dependent on the preparation methods that are used and the resulting film structures. Growth factors of the deposited film such as film thickness, deposition rate and quality of crystallites can be controlled by varying the solution pH, temperature and component concentrations of the bath.

The chemical bath deposition (CBD) process of the present technology offers many advantages over other well-known vapor phase synthetic routes for oxide films. For example, the chemical bath deposition process does not need a conductive substrate, which is required with electrodeposition techniques. This allows the deposition of a uniform and high-quality iridium oxide film onto non-conductive as well as conductive target substrates.

Another advantage of the chemical bath deposition of iridium oxide scheme is that it does not require a heating and vacuum system as required by reactive sputtering deposition and thermal decomposition techniques. The present methods also do not require high voltage equipment and works at room temperature, and therefore operation costs are low compared to existing processes. Moreover, the aspect ratio limitation of conventional deposition processes is overcome with CBD.

The chemical bath deposition methods were successfully used to fabricate IrOx thin films on flexible substrates to illustrate the methods. Iridium oxide is an attractive ceramic material for neurostimulation electrodes due to its desirable stability and biocompatibility, for example.

Iridium oxide films were fabricated by chemical bath deposition to show control over the film structure and functional characteristics and evaluate the film properties and performance at room temperature. Surface morphology, crystallinity, roughness, hydrophilicity, and charge storage capacity as well as biocompatibility of the films with different thicknesses were analyzed. The Iridium oxide films were also tested for cell viability to confirm film biocompatibility for further implantation applications.

In addition, iridium oxide films have also been explored in other applications on other fields such as catalysis, electrochromic devices and ferroelectric memories. Therefore, the development of the functional ceramic films shown here may also be adapted for use in other areas.

Further aspects of the technology described herein will be brought out in the following portions of the specification, wherein the detailed description is for the purpose of fully disclosing preferred embodiments of the technology without placing limitations thereon.

BRIEF DESCRIPTION OF THE SEVERAL VIEWS OF THE DRAWINGS

The technology described herein will be more fully understood by reference to the following drawings which are for illustrative purposes only:

FIG. 3A is a schematic cross-sectional view of the deposition of chromium/aluminum layers on to a handle silicon wafer.

FIG. 3B illustrates the deposition of a first polyimide layer over the aluminum layer of the structure of FIG. 3A.

FIG. 3C is an illustration of the step of applying a titanium/platinum layer on the first polyimide layer of FIG. 3B.

FIG. 3D illustrates the deposition of a second polyimide layer over the titanium/platinum layer and the first polyimide layer of FIG. 3C.

FIG. 3E illustrates the step of applying a patterned silicon dioxide layer on the second polyimide layer of FIG. 3D.

FIG. 3F depicts the structure after etching of the first and second polyimide layers of FIG. 3E.

FIG. 3G illustrated the detachment of the electrode array from the handle wafer by anodic metal dissolution of FIG. 3F.

FIG. 3H illustrates IrOx deposition of the electrode by the chemical bath deposition of FIG. 3G.

FIG. 3I illustrates the step of removal of the patterned silicon dioxide and any residual IrOx on the array of FIG. 3H.

DETAILED DESCRIPTION

Referring more specifically to the drawings, for illustrative purposes, embodiments of an apparatus and methods for thin film metal oxide electrode fabrication on flexible substrates are generally shown. Embodiments of the technology are described generally in FIG. 1 through FIG. 4 to illustrate the characteristics and functionality of the apparatus and system. It will be appreciated that the methods may vary as to the specific steps and sequence and the systems and apparatus may vary as to structural details without departing from the basic concepts as disclosed herein. The method steps are merely exemplary of the order that these steps may occur. The steps may occur in any order that is desired, such that it still performs the goals of the claimed technology.

Figure 1:
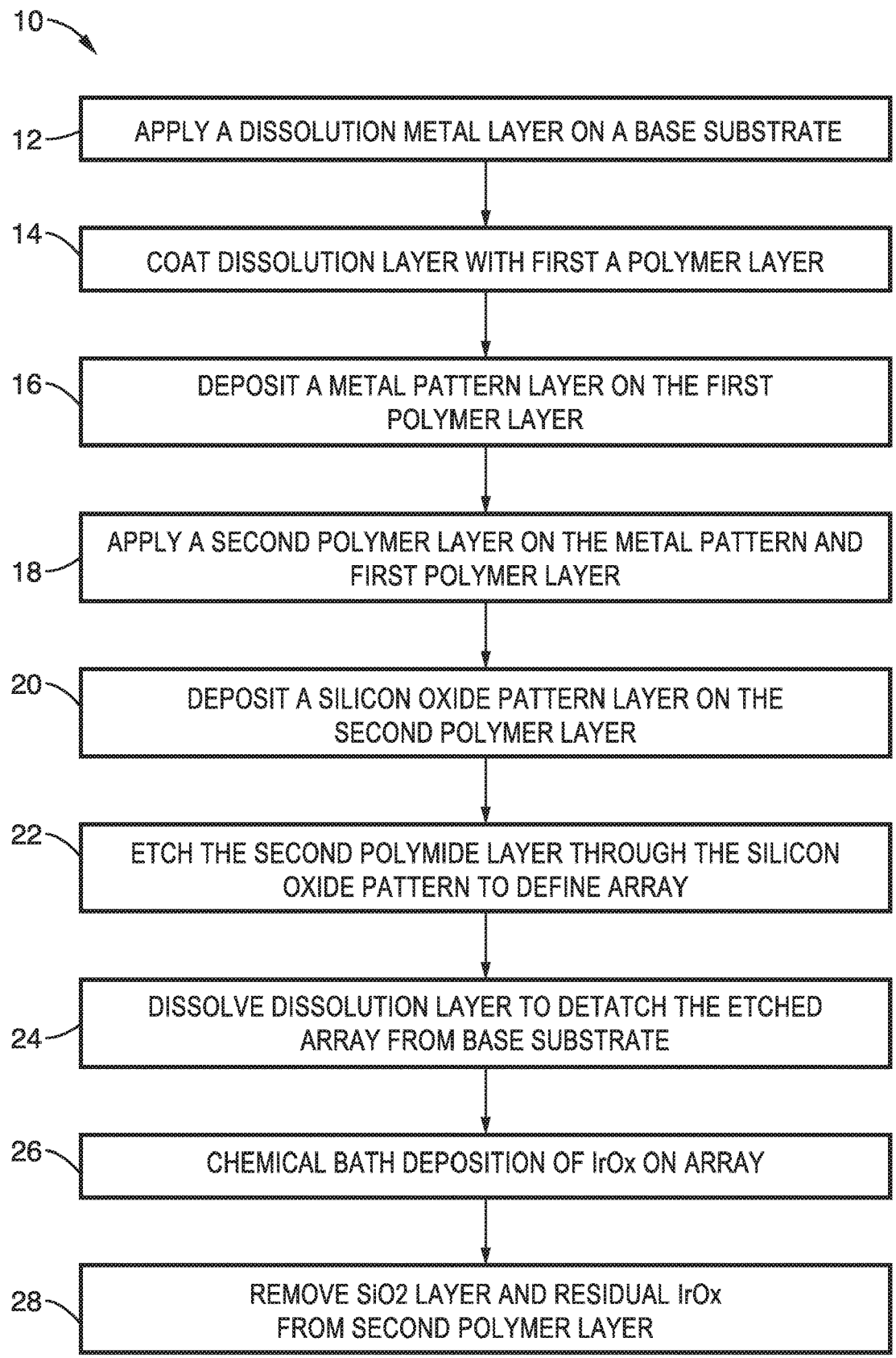
FIG. 1 is a functional block diagram of a method for metal oxide thin film electrode fabrication on a flexible polymeric substrate according to one embodiment of the technology.

Turning now to FIG. 1, method 10 for metal oxide thin film electrode fabrication on a flexible polymeric substrate is shown schematically. In the embodiment shown, the thin film metal oxide electrode fabrication has two major processes: 1) flexible thin film electrode structure formation; and 2) chemical bath deposition that allows control over metal oxide thin film growth factors such as film thickness, deposition rate and film quality with control over solution pH, temperature and bath component concentrations.

At block 12 of FIG. 1, a rigid or semi-rigid base substrate is provided such as a silicon sheet. A dissolution metal layer is then applied to the top surface of the base silicon sheet platform. In one embodiment, an optional inert metal layer is applied before to base silicon sheet before the formation of the dissolution metal layer on top of this protective metal layer. The preferred dissolution metal layer is aluminum. However, other layers performing the dissolution function as described can be used as well. Suitable protective layers include chromium.

A first polymer layer is applied to the top surface of the dissolution metal layer at block 14. The thickness of the first polymer layer can be selected based on the ultimate device design requirements. In one embodiment, several polymer layers are applied to form a laminate at block 14. The polymer layers are preferably formed from a polymer material that is efficiently and accurately etched with conventional etching techniques. While polyimide is preferred other polymer materials such as PMMA or PET can be used.

A conductive metal layer is then deposited on to the top surface of the first polymer layer at block 16. The deposited conductive metal layer can be solid or patterned. The conductive metal layer is preferably at least one or metal layers of a metal such as gold or platinum or a metal alloy such as titanium/platinum. Other conductive metals may also be used.

At block 18, at least one second polymer layer is applied over the first polymer layer and patterned metal layer. The second polymer layer is typically made from the same material as the first polymer layer, but need not be. In one embodiment, the second polymer layer is made of a different polymer material that is suitable and optimized for a desirable etching scheme.

Patterned silicon dioxide or other mask pattern layer is then deposited over the second polymer layer at block 20 to facilitate patterning of the first and second polymer layers at block 22 of FIG. 1. The etching of the second polymer layer at block 22 can be to any depth and dimensions such as down to the conductive metal layer or through both the first and second polymer layers to the metal dissolution layer. The pattern of silicon dioxide or other mask preferably defines an array. It will be seen that the etched pattern can be of any desirable electrode design.

The etched array can be separated from the base substrate with the dissolution of the dissolution layer at block 24 in this embodiment. The released etched array is then processed to place metal oxide layers at designated locations of exposed metal with a chemical bath deposition process at block 26. In one embodiment, the etched array remains attached with the base during the chemical bath deposition of metal oxide at block 26 and the array is detached later after the chemical bath deposition.

Figure 2:
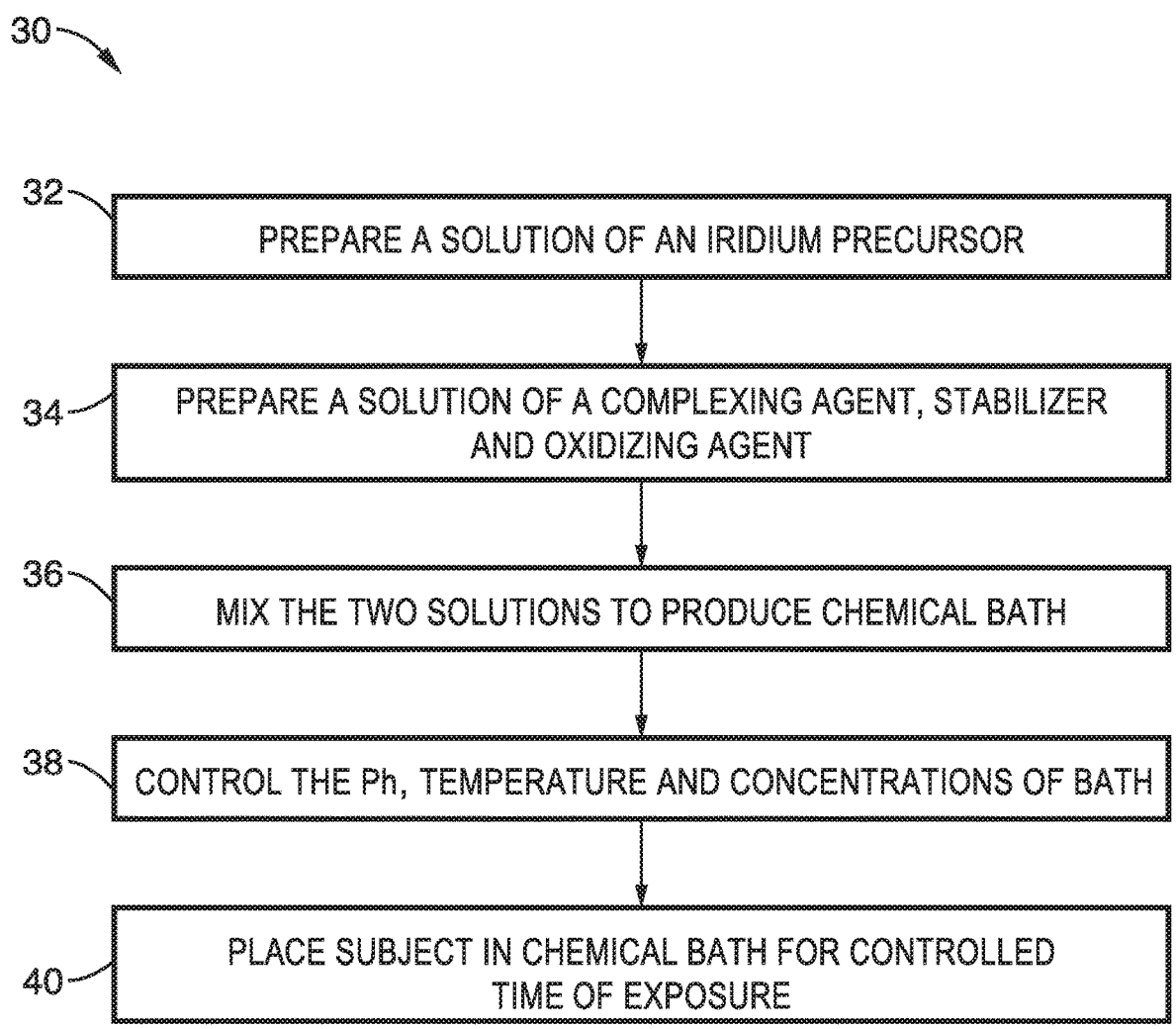
FIG. 2 is a functional block diagram of a method for metal oxide chemical bath deposition according to one embodiment of the technology.

Referring also to FIG. 2, one method 30 for chemical bath deposition of metal oxide is described that can be used at block 26 of FIG. 1. The chemical bath is preferably prepared by first providing a solution of at least one metal oxide precursor at block 32. At block 34 of FIG. 2, a second solution is prepared that contains one or more of a complexing agent, a stabilizer and an oxidizing agent. This second solution is then mixed with the solution of metal oxide precursor at block 36 to provide the chemical bath.

The pH, temperature and component concentrations in the resulting chemical bath of block 36 are controlled at block 38. For metal oxide films, the preparation conditions, starting materials and methods will determine the film structure, redox states, charge storage capacities, and impedances at the interface of the final layer that is deposited at block 26 of FIG. 1. The array or part of the array is placed in the bath for a controlled time of exposure that is selected to deposit a metal oxide layer of desired thickness and at desired locations at block 40 of FIG. 2. In one embodiment, all or part of the electrode is exposed to multiple bath events at block 40 to form multiple oxide layers.

After the chemical bath deposition at block 26, the silicon oxide mask layer and any residual metal oxide is removed from the top surface of the etched second polymer layer to complete the electrode at block 28 of FIG. 1.

Accordingly, the process flow design will allow the selective deposition of metal oxides at selected points on the body of the flexible electrode. For example, the metal oxide layer can be coated only onto the exposed conductive metal layer areas but not on to the entire device surface. In this way, it is possible to coat every individual electrode in one batch, and guarantee electrical isolation between each channel. In addition, the pads that typically provide external connections will not have metal oxide coverage, which can interfere with the soldering/bumping process, if only portions of the electrode body are placed in the chemical bath.

The technology described herein may be better understood with reference to the accompanying examples, which are intended for purposes of illustration only and should not be construed as in any sense limiting the scope of the technology described herein as defined in the claims appended hereto.

Example 1

In order to demonstrate the operational principles of the chemical bath deposition methods and devices, iridium oxide films were fabricated by chemical bath deposition to show control over the film structure and functional characteristics. The method of fabrication of iridium oxide films on a flexible electrode substrate as generally depicted in FIG. 1 and FIG. 2 was preformed and the film properties and film performance were evaluated.

Referring now to FIG. 3A to FIG. 3I, the process 42 of fabrication of a thin film polyimide electrode incorporating an IrOx chemical bath deposition of metal oxide on electrodes is depicted schematically in cross-section.

Figure 3A:
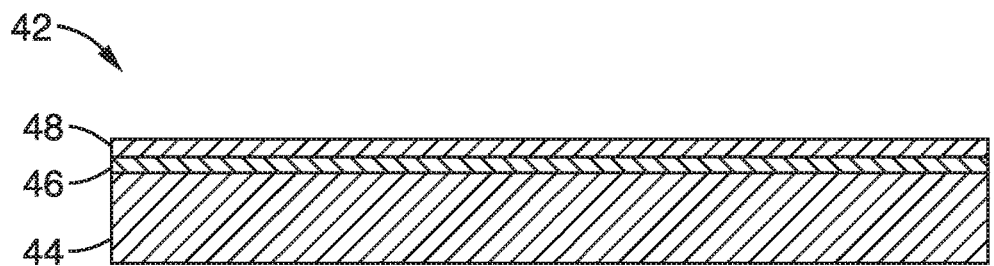
FIG. 3A to FIG. 3I depict an electrode fabrication process for IrOx thin film electrode fabrication on a polyimide substrate according to one embodiment of the technology.

In step (A) of FIG. 3A, a protective 200 nm chromium layer 46 was applied to a base platform of handle silicon 44 and a 500 nm aluminum dissolution layer 48 was applied to the chromium layer 46. The Chromium/Aluminum (200 nm/500 nm) layers 46, 48 were deposited by E-beam evaporated deposition (CHA Mark 40) on to the handle silicon wafer 44.

Figure 3B:
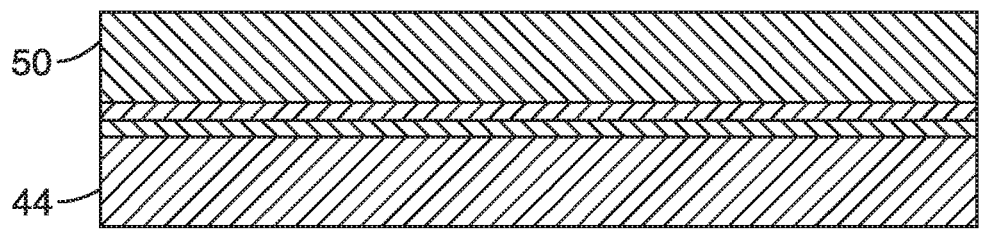

In step (B), a first polyimide layer 50 was applied over the surface of the aluminum layer 48 as shown in FIG. 3B. Here, a 4 μm polyimide (PI-2611, HD Microsystems) was spin-coated onto the wafer and cured in 350° C. for 30 minutes in a nitrogen-controlled oven to form full cross-link in the polyimide.

Figure 3C:
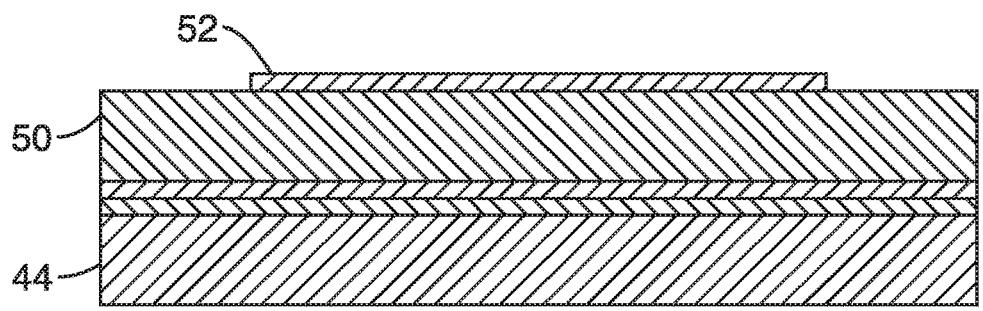

At step (C), a conductive metal layer 52 of a titanium and platinum was deposited on the first polyimide layer 50 as shown in FIG. 3C. The Titanium/Platinum (10 nm/200 nm) layer was defined and deposited using E-beam evaporated deposition (CHA Mark 40) using Lift-off to define the metal pattern.

Figure 3D:
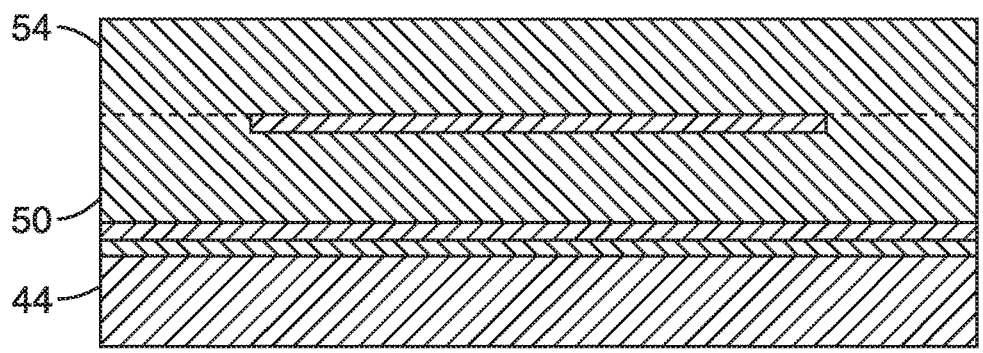

In step (D) illustrated in FIG. 3D, a second 4 μm polyimide (PI-2611, HD Microsystems) layer 54 was spin-coated onto the conductive layer 52 and first polyimide layer 50 of the wafer, and cured in 350° C. for 30 minutes in a nitrogen-controlled oven.

Figure 3E:
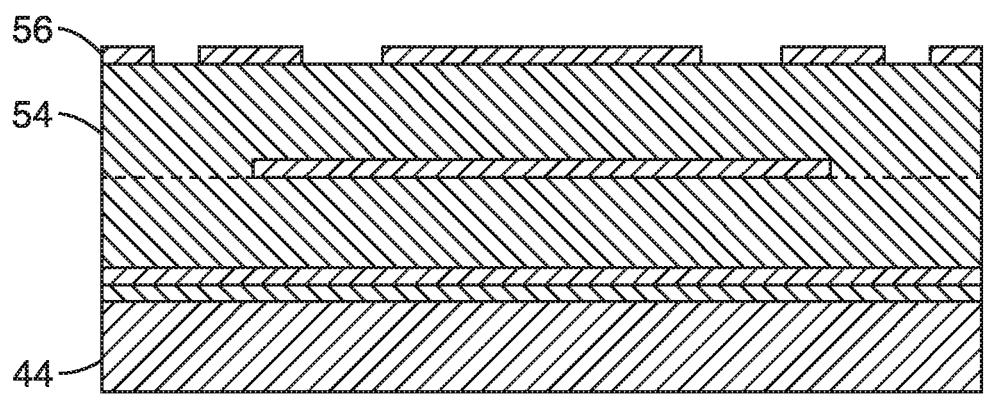

A mask layer 56 was applied at step (E) of a silicon dioxide (200 nm) film that was deposited using a DC sputter (Denton Discovery-550) as seen in FIG. 3E. The silicon oxide mask 56 had a defined pattern that was defined by a CHF3/Ar reactive ion etch (RIE) process using a plasma etcher (Oxford Plasmalab-80 Plus).

Figure 3F:
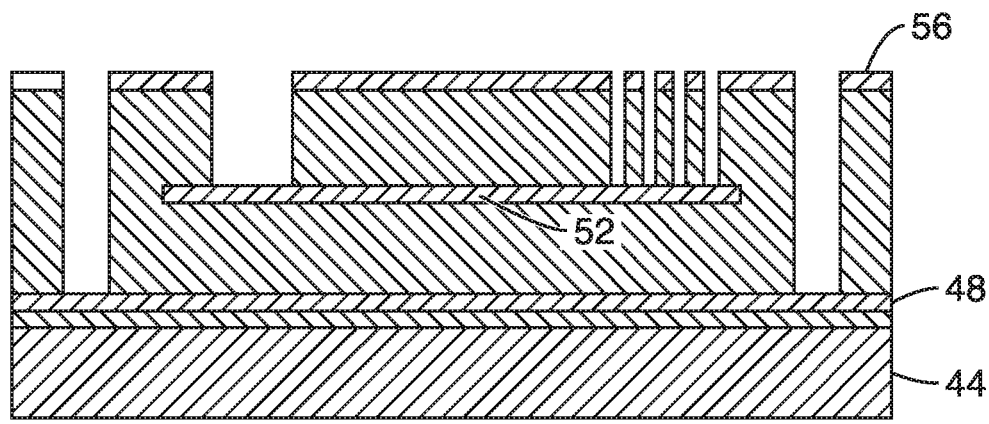

At step (F) of FIG. 3F, a pure oxygen plasma process was used to define the array shape as well as exposing the metal layer of electrodes and connector pads. Afterward, an extra oxygen/CF4 RIE process was utilized to remove the residual layer composed of the silicon containing active ingredient. The fluorine etching on platinum in the oxygen/CF4 RIE process roughened the platinum surface.

Figure 3G:
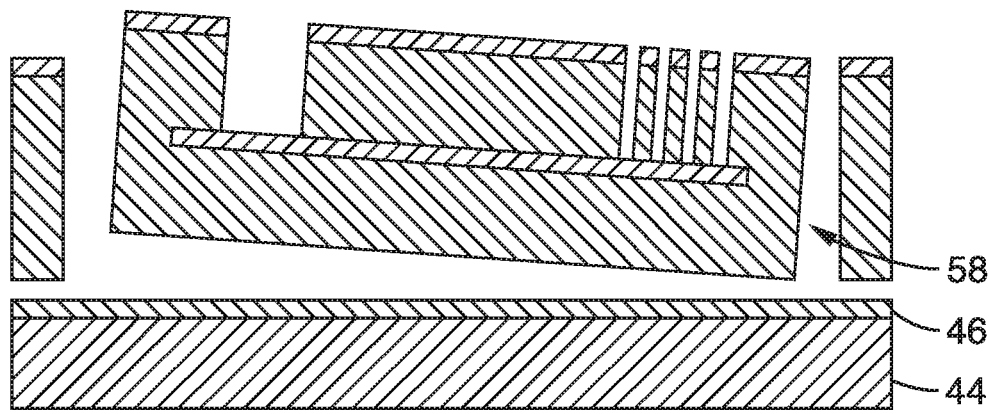

At step (G) of FIG. 3G, the electrode array(s) 58 were detached from the handle wafer 44 by anodic metal dissolution of the aluminum dissolution layer 48 in a 10 wt % sodium chloride solution. The anodic metal dissolution process dissolves the aluminum 48, leaving the chrome layer 46 on the silicon substrate surface, thus releasing the polyimide electrode arrays 58 from the substrate 44.

Figure 3H:
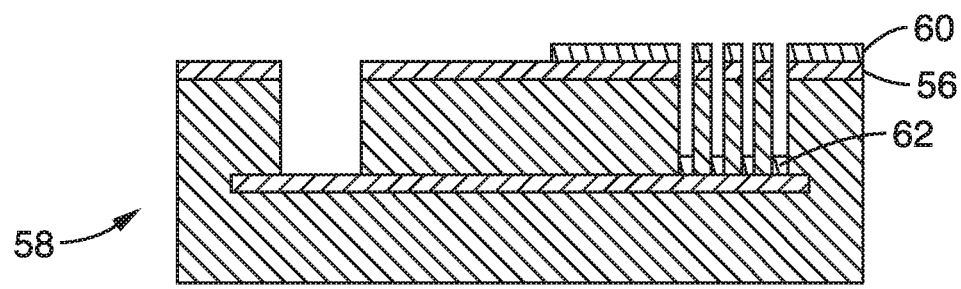

At step (H) of FIG. 3H, IrOx deposition on the array 58 was initialized by using the chemical bath deposition method.

The chemicals and processing conditions for the $IrO_2$ chemical bath deposition solution are listed in Table 1. The selected Iridium precursor was $Na_3IrCl_6 \cdot xH_2O$ which was measured and dissolved in deionized water. The $NaNO_2$ complexing agent, the NaOH stabilizer, and NaClO oxidizer were separately dissolved in deionized water. Thereafter, these three solutions were mixed together, becoming a transparent mixture. Then, the iridium precursor solution was added to the transparent mixture, resulting in a light yellowish solution with pH values between 12 and 13.

Finally, the device array 58 was pre-rinsed with deionized water to remove any contaminants and impurities and then immersed in the plating bath at 25° C. for 4 hours to allow the growth of IrO$_2$ (40~50 nm) selectively on the electrode surface. In this illustration, only the electrode part of the polyimide device was immersed in the chemical bath solution for deposition and therefore only half of the device array 58 was deposited with IrOx 60. In another embodiment, multiple layers were applied with multiple depositions.

Figure 3I:
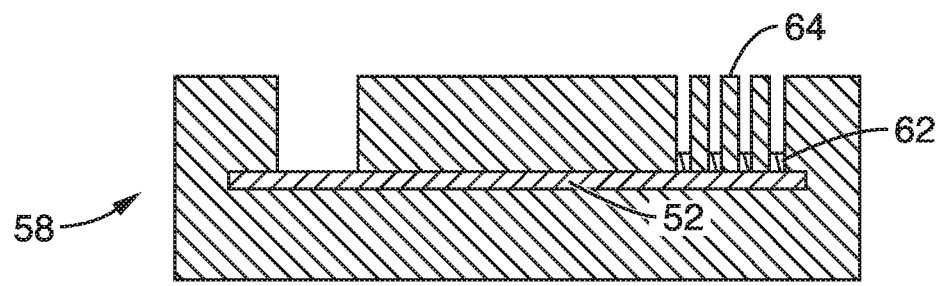

At step (I) shown in FIG. 3I, the chemical bath deposition was brought to an end. The strong base in the bath spontaneously and partially removed the SiO$_2$ pattern layer 56 on the top surface 64 of the second polyimide layer 54, such that only the electrode site 62 has IrOx deposition. Any residual IrOx deposited on the SiO$_2$ patterned layer was also removed.

Example 2

Iridium oxide films that were fabricated by chemical bath deposition were tested to demonstrate the functionality of the films and the electrode. Surface morphology, crystallinity, roughness, hydrophilicity, and charge storage capacity as well as biocompatibility of the films with different thicknesses were analyzed. The Iridium oxide films were also tested for cell viability to confirm film biocompatibility.

Surface morphology and film thickness were observed under a field-emission scanning electron microscope (FE-SEM; JEOL-JSM-6700F). An atomic force microscope (AFM; Bruker Innova) was used to determine the roughness of the films. The contact angle measurement (First Ten Angstroms PCS-1000B) was carried out to determine the hydrophilicity/hydrophobicity of the sample surface.

Analysis of the SEM images of the electrode after the deposition process and the EDS analysis, indicated that IrO$_2$ was deposited exclusively on the surface of platinum electrode. The device surface, covered by SiO$_2$, was unable to promote the seeding and growth of IrO$_2$ because the SiO$_2$ was susceptible to severe attack by the high alkalinity of the chemical bath. Table 2A shows the constituent materials found at the center of the electrode and Table 2B at the outer edge of the electrode.

Cyclic voltammetry (CV) was carried out in a phosphate buffered saline (PBS) electrolyte (0.15M NaCl solution) with the Jiehan potentiostat. The working electrodes were 1×1 cm$^2$ of the as-deposited structure with a thickness of 1 mm. A platinum sheet was used as a counter electrode, and an Ag/AgCl electrode as a reference electrode. The scan rate (Vs=dv/dt)=100 mV/s and the estimated water window≈–0.6 V~0.8V.

Figure 4:
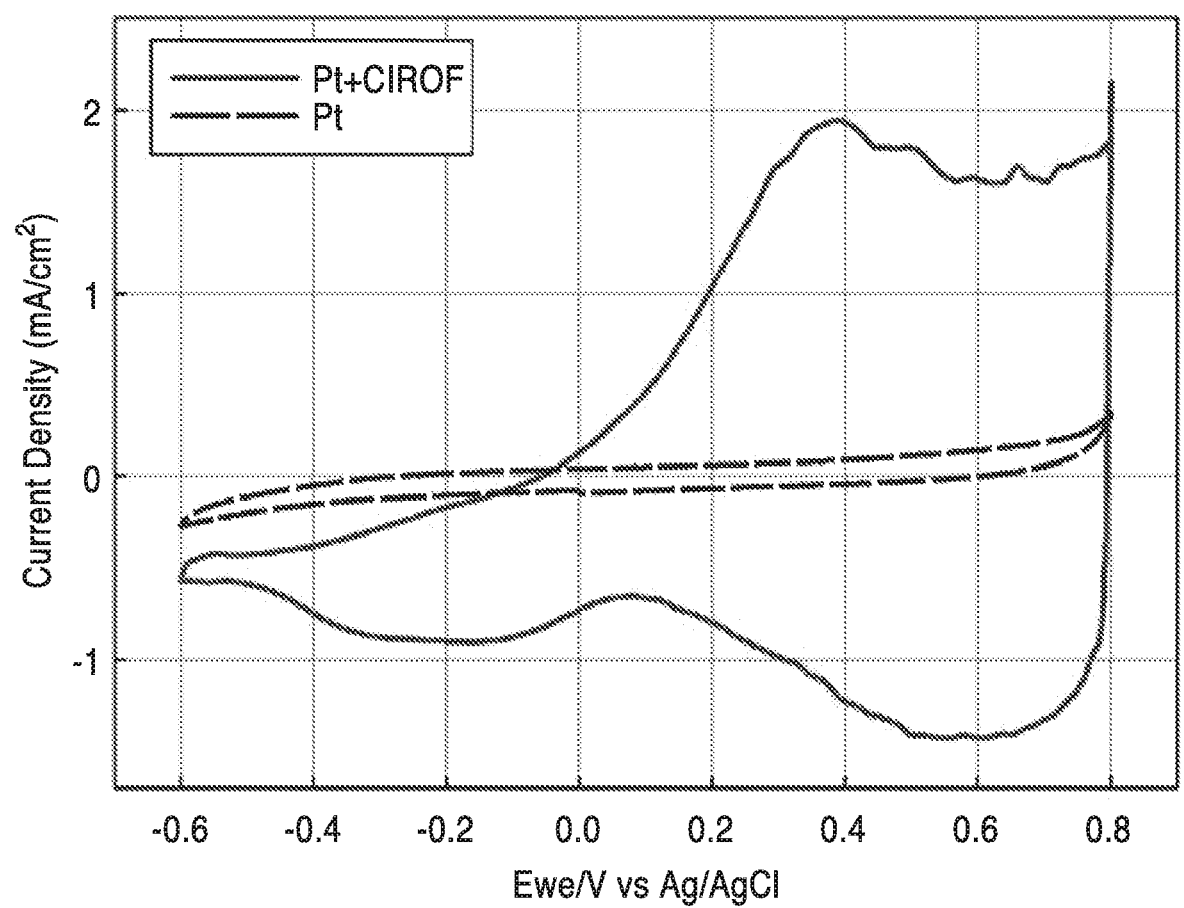
FIG. 4 is a cyclic voltammetry (CV) plot of a platinum electrode and an electrode with IrOx.

The CV plot is shown in FIG. 4. The solid traces that are centered show the original platinum electrode. The dashed traces show the platinum electrode with IrOx deposition. These results show that the electrode with IrOx coating has a significantly improved charge storage capability than the original platinum electrode.

It has become common practice to characterize the stimulation electrodes by measuring the cathodic charge storage capacity (CSC). The CSC was determined by integration of the cathodic current in a slow-sweep-rate cyclic voltammetry over a potential range that was just within the water electrolysis window (0.6 to 0.8 V at 50 mV$^{-1}$ for iridium oxide).

Embodiments of the present technology may be described herein with reference to flowchart illustrations of methods and systems according to embodiments of the technology, and/or procedures, algorithms, steps, operations, formulae, or other computational depictions, which may also be implemented as computer program products. In this regard, each block or step of a flowchart, and combinations of blocks (and/or steps) in a flowchart, as well as any procedure, algorithm, step, operation, formula, or computational depiction can be implemented by various means, such as hardware, firmware, and/or software including one or more computer program instructions embodied in computer-readable program code. As will be appreciated, any such computer program instructions may be executed by one or more computer processors, including without limitation a general purpose computer or special purpose computer, or other programmable processing apparatus to produce a machine, such that the computer program instructions which execute on the computer processor(s) or other programmable processing apparatus create means for implementing the function(s) specified.

Accordingly, blocks of the flowcharts, and procedures, algorithms, steps, operations, formulae, or computational depictions described herein support combinations of means for performing the specified function(s), combinations of steps for performing the specified function(s), and computer program instructions, such as embodied in computer-readable program code logic means, for performing the specified function(s). It will also be understood that each block of the flowchart illustrations, as well as any procedures, algorithms, steps, operations, formulae, or computational depictions and combinations thereof described herein, can be implemented by special purpose hardware-based computer systems which perform the specified function(s) or step(s), or combinations of special purpose hardware and computer-readable program code.

From the description herein, it will be appreciated that that the present disclosure encompasses multiple embodiments which include, but are not limited to, the following:

1. A method for producing biocompatible electrostimulation electrodes coated with metal oxide thin films, the method comprising: (a) applying a dissolution metal layer on a substrate; (b) coating a first polymer layer on the dissolution layer; (c) patterning a conductive metal layer on the first polymer layer; (d) applying a second polymer layer on the patterned metal layer and first polymer layer; (e) depositing a patterned mask layer on the second polymer layer; (f) etching the first polymer layer and the second polymer layer through the patterned mask layer; (g) dissolving the dissolution metal layer to detach an etched array from the base substrate; (h) applying a metal oxide film at selected locations on the array with chemical bath deposition; and (i) removing the mask layer to complete the electrode array.

2. The method of any preceding or following embodiment, further comprising: depositing a protective metal layer between the base and the dissolution layer.

3. The method of any preceding or following embodiment, wherein the protective layer comprises chromium and the dissolution layer comprises aluminum.

4. The method of any preceding or following embodiment, wherein the first and second polymer layers comprise polyimide.

5. The method of any preceding or following embodiment, wherein the conductive metal layer is at least one metal selected from the group of metals consisting of titanium, platinum, gold and copper.

6. The method of any preceding or following embodiment, wherein the mask layer comprises silicon dioxide.

7. The method of any preceding or following embodiment, wherein the chemical path deposition step comprises:

(a) preparing a solution of a metal oxide precursor; (b) preparing a solution of a complexing agent, a stabilizing agent and an oxidizing agent; (c) mixing the metal oxide precursor solution with the solution of complexing, stabilizing and oxidizing agents to produce a chemical bath; and (d) depositing metal oxide on parts of the etched array placed in the chemical bath.

8. The method of any preceding or following embodiment, further comprising: controlling pH, temperature and component concentrations of the chemical bath.

9. The method of any preceding or following embodiment, further comprising: controlling a time of exposure of the etched array to the chemical bath.

10. A method for producing biocompatible electrostimulation electrodes coated with metal oxide thin films, the method comprising: (a) providing an electrode with one or more metal surfaces; (b) preparing a chemical bath by performing steps comprising: (i) preparing a solution of a metal oxide precursor; (ii) preparing a solution of a complexing agent, a stabilizing agent and an oxidizing agent; and (iii) mixing the metal oxide precursor solution with the solution of complexing, stabilizing and oxidizing agents to produce a chemical bath; and (c) placing metal surfaces of the electrode in the chemical bath thereby depositing metal oxide on the electrode metal surfaces.

11. The method of any preceding or following embodiment, further comprising: controlling pH, temperature and component concentrations of the chemical bath.

12. The method of any preceding or following embodiment, further comprising: controlling a time of exposure of the electrode metal surfaces to the chemical bath.

13. The method of any preceding or following embodiment, further comprising: placing metal surfaces of the electrode in the chemical bath multiple times thereby depositing metal oxide on the electrode metal surfaces in multiple layers.

14. The method of any preceding or following embodiment, wherein the electrode metal surface is a metal selected from the group of metals consisting of titanium, platinum and gold.

15. The method of any preceding or following embodiment, wherein the metal oxide precursor comprises $Na_3IrCl_6 \cdot xH_2O$, the complexing agent comprises $NaNO_2$, and the oxidizing agent comprises NaClO.

16. The method of any preceding or following embodiment, wherein the metal oxide coating the electrode comprises iridium oxide.

17. A method for producing flexible electrodes coated with $IrO_2$ oxide, the method comprising: (a) providing a silicon base with a top surface layer of chromium; (b) applying a dissolution metal layer of aluminum on the chromium layer; (c) coating the dissolution layer with a first polymer layer; (d) patterning a conductive metal layer on the first polymer layer; (e) applying a second polymer layer on the patterned metal layer and first polymer layer; (f) depositing a patterned mask layer on the second polymer layer; (g) etching the first polymer layer and the second polymer layer through the patterned mask layer; (h) dissolving the dissolution metal layer to detach an etched array from the base substrate; (i) preparing a chemical bath by performing steps comprising: (i) preparing a solution of an $IrO_2$ oxide precursor; (ii) preparing a solution of a complexing agent, a stabilizing agent and an oxidizing agent; and (iii) mixing the $IrO_2$ oxide precursor solution with the solution of complexing, stabilizing and oxidizing agents to produce a chemical bath; (j) applying a $IrO_2$ oxide film on selected etched locations on the etched array with chemical bath deposition; and (k) removing the mask layer to complete the electrode array.

18. The method of any preceding or following embodiment, wherein the first and second polymer layers comprise polyimide.

19. The method of any preceding or following embodiment, wherein the electrode metal surface is a metal selected from the group of metals consisting of titanium, platinum and gold.

20. The method of any preceding or following embodiment, wherein the $IrO_2$ oxide precursor comprises $Na_3IrCl_6 \cdot xH_2O$, the complexing agent comprises $NaNO_2$, and the oxidizing agent comprises NaClO.

21. A method for selective Iridium Oxide (IrOx) deposition on a flexible substrate.

22. A flexible thin film Iridium Oxide (IrOx) electrode fabricated by selective Iridium Oxide (IrOx) deposition on a flexible substrate.

23. A thin film Iridium Oxide (IrOx) electrode, comprising: a flexible polyimide structure having a buried metallic layer; an array of electrodes defined through the polyimide structure to the buried metallic layer; and a coating of Iridium Oxide (IrOx) upon the buried metallic layer through defined array of electrodes.

24. The electrode of any preceding or following embodiment, wherein the buried metallic layer comprises titanium or platinum.

25. A method for selective chemical bath deposition of Iridium Oxide (IrOx) on a thin film polyimide electrode structure, the method comprising: fabricating a flexible thin film polyimide structure having a buried metallic layer which is exposed through the thin film polyimide structure in response to defining an electrode, electrodes, or electrode array; and performing a chemical bath deposition of Iridium Oxide (IrOx) to coat the buried metallic layer at the electrode, electrodes, or electrode array.

26. The method of any preceding or following embodiment, wherein the thin film polyimide structure is deposited over an aluminum layer of a handle wafer.

27. The method of any preceding or following embodiment, wherein during the chemical bath deposition of Iridium Oxide (IrOx), the Iridium Oxide coats only the exposed areas of the buried metallic layer at the electrode, electrodes, or electrode array, but not the entire device surface.

28. The method of any preceding or following embodiment, wherein during the chemical bath deposition of Iridium Oxide (IrOx), the Iridium Oxide coats only the exposed metal areas of the buried metallic layer at the electrode, electrodes, or electrode array in a single batch, while ensuring isolation between electrode channels.

29. The method of any preceding or following embodiment, wherein the chemical bath deposition of Iridium Oxide (IrOx) on the buried metallic layer at the electrode, electrodes, or electrode array, is a selective deposition in which pads for external connections are not covered with IrOx which could interfere with a soldering/bumping process.

30. The method of any preceding or following embodiment, wherein the fabricating a thin film polyimide structure comprises: depositing chromium/aluminum by E-beam evaporated deposition on a wafer; spin coating the wafer with polyimide and curing it under sufficient heat to form cross-linking in the polyimide; defining and depositing titanium/platinum using E-beam evaporated deposition to define a buried metallic layer; spin coating an additional layer of polyimide onto the wafer and curing it under sufficient heat to form cross-linking in the polyimide; depositing a silicon dioxide film and defining its area using an etching process; defining a shape for an electrode, electrodes or electrode array through the polyimide to the metallic layer using an oxygen plasma process; removing a residual layer comprising silicon containing active ingredient; and detaching the electrode, electrodes, or electrode array from the wafer, by dissolving the aluminum to release the polyimide structure and its electrode, electrodes, or electrode array.

31. The method of any preceding or following embodiment, wherein the buried metallic layer is deposited in a desired pattern.

32. The method of any preceding or following embodiment, wherein the chemical bath deposition of Iridium Oxide (IrOx) comprises: performing Iridium Oxide deposition within a chemical bath in which only an electrode, electrode, or electrode array portion are immersed for deposition and thus coated with IrOx; and partially removing $SiO_2$ on top of the polyimide structure whereby only the electrode, electrodes, or electrode array are coated with IrOx deposition.

As used herein, the singular terms "a," "an," and "the" may include plural referents unless the context clearly dictates otherwise. Reference to an object in the singular is not intended to mean "one and only one" unless explicitly so stated, but rather "one or more."

As used herein, the term "set" refers to a collection of one or more objects. Thus, for example, a set of objects can include a single object or multiple objects.

As used herein, the terms "substantially" and "about" are used to describe and account for small variations. When used in conjunction with an event or circumstance, the terms can refer to instances in which the event or circumstance occurs precisely as well as instances in which the event or circumstance occurs to a close approximation. When used in conjunction with a numerical value, the terms can refer to a range of variation of less than or equal to ±10% of that numerical value, such as less than or equal to ±5%, less than or equal to ±4%, less than or equal to ±3%, less than or equal to ±2%, less than or equal to ±1%, less than or equal to ±0.5%, less than or equal to ±0.1%, or less than or equal to ±0.05%. For example, "substantially" aligned can refer to a range of angular variation of less than or equal to ±10°, such as less than or equal to ±5°, less than or equal to ±4°, less than or equal to ±3°, less than or equal to ±2°, less than or equal to ±1°, less than or equal to ±0.5°, less than or equal to ±0.1°, or less than or equal to ±0.05°.

Additionally, amounts, ratios, and other numerical values may sometimes be presented herein in a range format. It is to be understood that such range format is used for convenience and brevity and should be understood flexibly to include numerical values explicitly specified as limits of a range, but also to include all individual numerical values or sub-ranges encompassed within that range as if each numerical value and sub-range is explicitly specified. For example, a ratio in the range of about 1 to about 200 should be understood to include the explicitly recited limits of about 1 and about 200, but also to include individual ratios such as about 2, about 3, and about 4, and sub-ranges such as about 10 to about 50, about 20 to about 100, and so forth.

Although the description herein contains many details, these should not be construed as limiting the scope of the disclosure but as merely providing illustrations of some of the presently preferred embodiments. Therefore, it will be appreciated that the scope of the disclosure fully encompasses other embodiments which may become obvious to those skilled in the art.

All structural and functional equivalents to the elements of the disclosed embodiments that are known to those of ordinary skill in the art are expressly incorporated herein by reference and are intended to be encompassed by the present claims. Furthermore, no element, component, or method step in the present disclosure is intended to be dedicated to the public regardless of whether the element, component, or method step is explicitly recited in the claims. No claim element herein is to be construed as a "means plus function" element unless the element is expressly recited using the phrase "means for". No claim element herein is to be construed as a "step plus function" element unless the element is expressly recited using the phrase "step for".

TABLE 1

Chemicals and processing conditions for the chemical bath deposition of $IrO_2$

| Bath | Chemicals |
|---|---|
| Precursor | $Na_3IrCl_6 \cdot xH_2O$ |
| Complexing agent | $NaNO_2$ |
| Stabilizer & complexing agent | NaOH |
| Oxidizing agent | NaClO |
| pH | 12-13 |
| Temperature | 25° C. |

TABLE 2A

| Element | Weight % | Atomic % |
|---|---|---|
| C K | 12.58 | 35.79 |
| O K | 24.91 | 53.21 |
| Ir M | 15.30 | 2.72 |
| Pt M | 47.21 | 8.27 |
| Totals | 100.00 | 100.00 |

TABLE 2B

| Element | Weight % | Atomic % |
|---|---|---|
| C K | 74.26 | 79.35 |
| O K | 25.74 | 20.65 |
| Totals | 100.00 | 100.00 |

What is claimed is:

1. A method for producing biocompatible electrostimulation electrodes coated with metal oxide thin films, the method comprising:
   (a) applying a dissolution metal layer on a substrate;
   (b) coating a first polymer layer on the dissolution layer;
   (c) patterning a conductive metal layer on the first polymer layer;
   (d) applying a second polymer layer on the patterned metal layer and first polymer layer;
   (e) depositing a patterned mask layer on the second polymer layer;
   (f) etching the first polymer layer and the second polymer layer through the patterned mask layer;
   (g) dissolving the dissolution metal layer to detach an etched array from the base substrate;
   (h) applying a metal oxide film at selected locations on the array with chemical bath deposition; and (i) removing the mask layer to complete the electrode array.

2. The method of claim 1, further comprising:
depositing a protective metal layer between the base and the dissolution layer.

3. The method of claim 2, wherein said protective layer comprises chromium and said dissolution layer comprises aluminum.

4. The method of claim 1, wherein said first and second polymer layers comprise polyimide.

5. The method of claim 1, wherein said conductive metal layer is at least one metal selected from the group of metals consisting of titanium, platinum and gold.

6. The method of claim 1, wherein said mask layer comprises silicon dioxide.

7. The method of claim 1, wherein said chemical path deposition step comprises:
  (a) preparing a solution of a metal oxide precursor;
  (b) preparing a solution of a complexing agent, a stabilizing agent and an oxidizing agent;
  (c) mixing the metal oxide precursor solution with the solution of complexing, stabilizing and oxidizing agents to produce a chemical bath; and
  (d) depositing metal oxide on parts of the etched array placed in the chemical bath.

8. The method of claim 7, further comprising: controlling pH, temperature and component concentrations of the chemical bath.

9. The method of claim 7, further comprising:
controlling a time of exposure of the etched array to the chemical bath.

10. A method for producing flexible electrodes coated with $IrO_2$ oxide, the method comprising:
  (a) providing a silicon base with a top surface layer of chromium;
  (b) applying a dissolution metal layer of aluminum on the chromium layer;
  (c) coating the dissolution layer with a first polymer layer;
  (d) patterning a conductive metal layer on the first polymer layer;
  (e) applying a second polymer layer on the patterned metal layer and first polymer layer;
  (f) depositing a patterned mask layer on the second polymer layer;
  (g) etching the first polymer layer and the second polymer layer through the patterned mask layer;
  (h) dissolving the dissolution metal layer to detach an etched array from the base substrate;
  (i) preparing a chemical bath by performing steps comprising:
    (i) preparing a solution of an $IrO_2$ oxide precursor;
    (ii) preparing a solution of a complexing agent, a stabilizing agent and an oxidizing agent; and
    (iii) mixing the $IrO_2$ oxide precursor solution with the solution of complexing, stabilizing and oxidizing agents to produce a chemical bath;
  (j) applying a $IrO_2$ oxide film on selected etched locations on the etched array with chemical bath deposition; and
  (k) removing the mask layer to complete the electrode array.

11. The method of claim 10, wherein said first and second polymer layers comprise polyimide.

12. The method of claim 10, wherein said electrode metal surface is a metal selected from the group of metals consisting of titanium, platinum and gold.

13. The method of claim 10, wherein said $IrO_2$ oxide precursor comprises $Na_3IrCl_6 \cdot xH_2O$, said complexing agent comprises $NaNO_2$, and said oxidizing agent comprises $NaClO$.

* * * * *